US00PP09381P

United States Patent [19]

Schumann

[11] Patent Number: Plant 9,381

[45] Date of Patent: Nov. 21, 1995

[54] GERANIUM PLANT NAMED FISFLORI

[75] Inventor: Ingeborg Schumann, Albstadt, Germany

[73] Assignee: Florfis, AG, Binningen, Switzerland

[21] Appl. No.: 360,341

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisflori, particularly characterized by the combined features of bluish pink flower color with a white base on the upper petals, dark green foliage with very weak zonation, medium plant habit, and early flower response.

1 Drawing Sheet

The present invention comprises a new and distinct cultivar of geranium, botanically known as *Pelargonium, zonale l'Hert,* and hereinafter referred to by the cultivar name Fisflori.

Fisflori is a product of a planned breeding program which had the objective of creating new geranium cultivars with pink flower color, dark green foliage, and early spring flower response.

Fisflori was originated from a hybridization made by inventor Ingeborg Schumann in a controlled breeding program in Galdar, Gran Canaria, Spain in 1987. The female parent was a hybrid produced from a cross between the cultivar Rospen, characterized by violet-pink semi-double flowers, compact plant habit and foliage with zonation, and Blues (U.S. Plant Pat. No. 5,373), characterized by pink flowers with red markings and low plant habit. The male parent of Fisflori was Fisrix, disclosed in U.S. Plant Pat. No. 7,422, and characterized by its single light pink flowers with purple eyes, and dark green foliage.

Fisflori was discovered and selected as one flowering plant within the progeny of the stated cross by Ingeborg Schumann in 1988 in a controlled environment in Galdar, Gran Canaria, Spain.

The first act of asexual reproduction of Fisflori was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989, and continuing thereafter, has demonstrated that the combination of characteristics as herein disclosed for Fisflori are firmly fixed and are retained through successive generations of asexual reproduction.

Fisflori has not been observed under all possible environmental conditions. The phenotype may vary significantly with variations in environment such as temperature, light intensity and daylength without, however, any variation of genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisflori, which, in combination, distinguish this geranium as a new and distinct cultivar:

1. Bluish pink flower color, with the upper petals having a white base.
2. Dark green foliage with very weak zonation.
3. Medium plant habit.
4. Early spring flower response.

Of the many commercial cultivars known to the present inventor, the most similar in comparison to Fisflori is Auralia. Reference is made to attached Chart A which compares certain characteristics of Fisflori to those same characteristics of Auralia. In general comparison to Auralia, Fisflori has a somewhat lighter flower color and a more vigorous growth habit.

The accompanying color photographic drawing shows typical flower and foliage characteristics of Fisflori, with colors being as true as possible with illustrations of this type.

In the following description, color references are made to The Royal Horticultural Society (R.H.S.) Colour Chart. The color values were determined indoors in May from plants grown indoors in Hillscheid, Federal Republic of Germany.

Classification:

*Botanical.*—A hybrid of the species *Pelargonium l'Hert.*

*Commercial.*—Zonal geranium, cv., Fisflori.

INFLORESCENCE

Umbel:

*Shape.*—Semi-spherical.

*Average diameter.*—90 mm.

*Average depth.*—45 mm.

*Peduncle length.*—180 mm.

*Pedicel length.*—25 mm.

*Pedicel color.*—Dark red.

*Number of flowers per umbel.*—30–40.

Corolla:

*Average diameter.*—42 mm.

*Form.*—Semi-double.

*Number of petals.*—6–8.

*Number of petaloids.*—1–3.

*Color (general tonality from a distance of three meters).*—Pink with a bluish tint.

*Color of upper petals.*—68B.

*Color of lower petals.*—68A–B.

*Markings on upper petals.*—Medium size white eye at the base of the petals.

*Color of lower surface of petals.*—On mature petals, 68B–D, with red veins; on young petals, color is very light pink.

*Color of sepals.*—Green with anthocyanin, partly red.

*Number of sepals.*—5.

Bud:

*Shape.*—Elliptic.

*Color (adaxial).*—Green with, anthocyanin at the base.

*Color (abaxial).*—Pink to violet-pink.

Reproductive organs:

*Androecium.*—4–6 anthers, not all of them fertile; orange pollen.

*Gynoecium.*—5–6 lobed stigma, pink style and stigma.

Spring flowering response period: In Hillscheid, Federal Republic of Germany, in 1993 plants had on average 1.2 flowers opened 10 weeks after planting of unrooted cuttings.

Outdoor flower production: The flower count in 1992 in Hillscheid, Federal Republic of Germany was between 40 and 45 flowers per plant for May through August observation period.

Durability: Shatter resistance good.

PLANT

Foliage:

*Form.*—Kidney-shaped.

*Margin.*—Bicrenated.

*Size of leaf.*—10–12 cm.

*Color of upper surface.*—Dark green, approximately 137A.

*Color (zonation).*—Deeper green; weak and not always visible, approximately 147A.

*Tolerance of botrytis.*—Average.

General appearance and form:

*Internode length.*—20–30 mm.

*Branching pattern.*—2.6 branches per week.

*Height.*—36 cm, in September based on 32 week old plants.

CHART A

| CHARACTERISTICS | FISFLORI | AURALIA |
|---|---|---|
| Flower color, upper petals | 68B | 68A |
| Pedicel color | Dark red | Light red |
| Size of white eye at base of petals | Medium | Small |
| Plant habit | Medium, compact | Short, compact |

I claim:

1. A new and distinct cultivar of geranium plant named Fisflori, as illustrated and described.

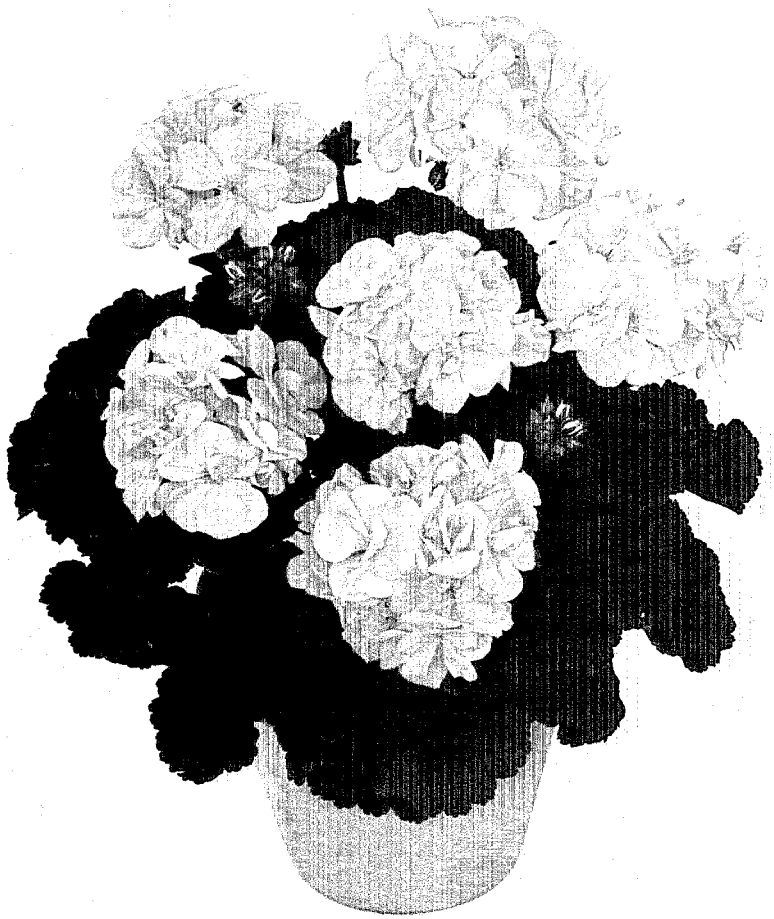

* * * * *